US012569133B2

(12) United States Patent
Kano et al.

(10) Patent No.: US 12,569,133 B2
(45) Date of Patent: Mar. 10, 2026

(54) OPTICAL SYSTEM AND INSPECTION APPARATUS

(71) Applicant: CANON KABUSHIKI KAISHA, Tokyo (JP)

(72) Inventors: Hiroto Kano, Tochigi (JP); Tokuji Takizawa, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 968 days.

(21) Appl. No.: 17/746,131

(22) Filed: May 17, 2022

(65) Prior Publication Data

US 2022/0378289 A1     Dec. 1, 2022

(30) Foreign Application Priority Data

May 28, 2021     (JP) ................................. 2021-089810

(51) Int. Cl.
| | |
|---|---|
| *A61B 3/14* | (2006.01) |
| *A61B 3/00* | (2006.01) |
| *A61B 3/113* | (2006.01) |

(52) U.S. Cl.
CPC .............. *A61B 3/14* (2013.01); *A61B 3/0008* (2013.01); *A61B 3/0091* (2013.01); *A61B 3/113* (2013.01)

(58) Field of Classification Search
CPC ....... A61B 3/14; A61B 3/0008; A61B 3/0091; A61B 3/113; A61B 3/1025
See application file for complete search history.

(56) References Cited

U.S. PATENT DOCUMENTS

| | | | |
|---|---|---|---|
| 10,154,164 B2 | 12/2018 | Kano | |
| 10,412,245 B2 | 9/2019 | Takizawa et al. | |
| 10,849,497 B2 | 12/2020 | Winsor et al. | |
| 2004/0105077 A1* | 6/2004 | Kim ..................... | G02B 27/123 353/31 |
| 2017/0227350 A1* | 8/2017 | Sarunic .............. | G01B 9/02063 |
| 2020/0257109 A1 | 8/2020 | Kano | |

* cited by examiner

*Primary Examiner* — James C. Jones

(74) *Attorney, Agent, or Firm* — Carter, DeLuca & Farrell LLP

(57) ABSTRACT

An optical system includes a lens unit configured to form a first intermediate image by using light from a light source, a first optical element configured to transmit the light from the first intermediate image and to move to rotationally scan a target, and a second optical element configured to guide the light from the first optical element to the target.

21 Claims, 4 Drawing Sheets

OPTICAL SYSTEM AND INSPECTION APPARATUS

BACKGROUND OF THE INVENTION

Field of the Invention

The present invention relates to an optical system and an inspection apparatus.

Description of the Related Art

It has been known that a central fovea (pit) is located at a center of a macula of a retina of an eye and the best vision is provided around the central fovea. It has also been known that where a subject is staring (fixation state) can be measured by detecting a birefringence state of a nerve fiber around the central fovea.

U.S. Pat. No. 10,849,497 discloses an ophthalmic neural scanner apparatus (inspection apparatus) including a projection apparatus configured to project a projected image onto a retina of an eye and a photodetector configured to capture a reflected image reflected by the retina, the reflected image indicating the fixation state of the eye. In this projection apparatus, light from a laser light source passes through an aperture of a toric mirror, is reflected by a spinning tilted mirror for generating a ring image, returns to the toric mirror, and enters the eye.

The ophthalmic neural scanner apparatus disclosed in U.S. Pat. No. 10,849,497 uses the spinning tilted mirror (decentered mirror) to generate the ring image. However, in a case where a spinning tilted mirror is used, it is necessary to use a large scanning mechanism that makes the spinning tilted mirror perform scanning and to dispose the spinning tilted mirror at a position away from the toric mirror. This increases a size of the ophthalmic neural scanner apparatus.

SUMMARY OF THE INVENTION

The present invention provides a small optical system and an inspection apparatus.

An optical system according to one aspect of embodiments of the present disclosure includes a lens unit configured to form a first intermediate image by using light from a light source, a first optical element configured to transmit the light from the first intermediate image and to move to rotationally scan a target, and a second optical element configured to guide the light from the first optical element to the target.

An inspection apparatus according to another aspect of embodiments of the present disclosure includes the above optical system and a detector configured to detect reflected light from the target.

Further features of the present invention will become apparent from the following description of exemplary embodiments with reference to the attached drawings.

DESCRIPTION OF THE EMBODIMENTS

Referring now to the accompanying drawings, a description will be given of embodiments according to the present invention.

An optical system according to each example is used, for example, as a projection optical system of an inspection apparatus (fixation measuring apparatus) that inspects where a subject's eye is staring (fixation state). However, in each example, a target (subject to be inspected) is not limited to the subject's eye (eyeball), and the present disclosure is applicable to targets other than the subject's eye.

The optical system according to each example includes a relay lens unit (lens unit) that forms an intermediate image (first intermediate image) IM1 by using light from a light source, a first optical element that transmits the light from the intermediate image IM1 and moves so that rotational scanning is performed on the target (moves to rotationally scan the target), and a second optical element that guides the light from the first optical element to the target. That is, the optical system according to each example is configured so that the intermediate image IM1 is formed by once imaging a light beam from the light source and no reflective surface is included on a projection surface side (target side) of the intermediate image IM1 in order that the light beam is transmitted through all the path to a projection surface PP (target). In the optical system according to each example, each optical element is properly configured and placed so that the light beam is properly incident on a retina of one or both eyes of a subject. Therefore, according to each example, rotational scanning using a light beam is performed by using an optical element that transmits the light beam, and hence it is possible to shorten an optical path length and to provide a small optical system and a small inspection apparatus.

The configuration of the optical system according to each example is described below in detail.

EXAMPLE 1

Figure 1:
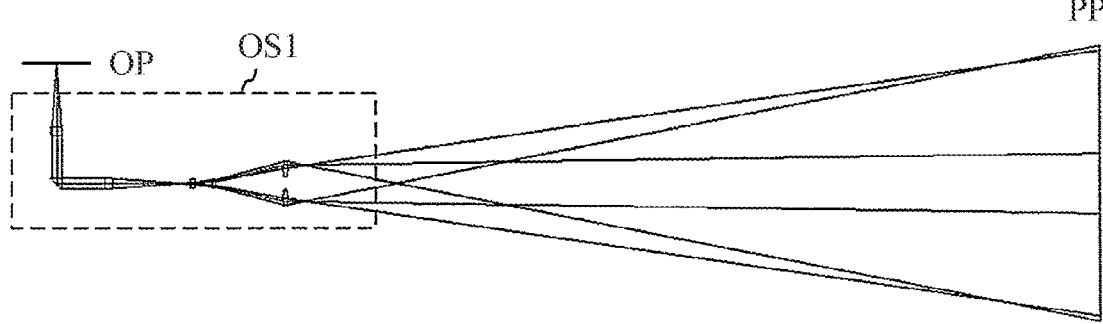
FIG. 1 is an optical path diagram from an object surface to a projection surface via an optical system according to Example 1.
Figure 2:
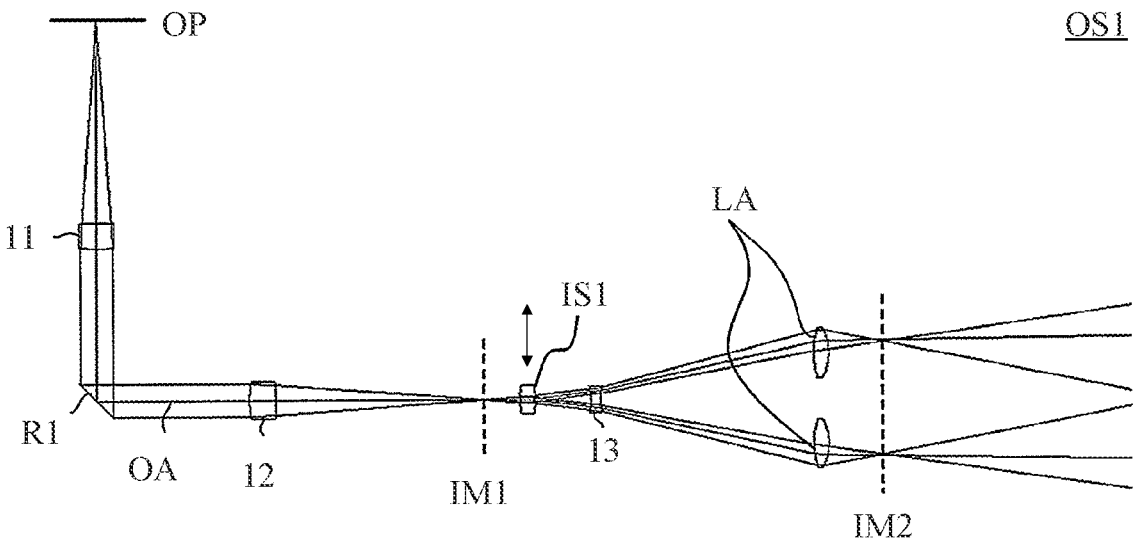
FIG. 2 is a sectional view of an optical system according to Example 1.

First, an optical system OS1 according to Example 1 of the present invention is described with reference to FIGS. 1 and 2. FIG. 1 is an optical path diagram from an object surface OP to a projection surface PP via an optical system OS1. FIG. 2 is a sectional view of the optical system OS1.

The optical system OS1 includes, in an order from an object surface side to a projection surface side (target side), a lens (first lens) 11, a reflective surface R1, a lens (second lens) 12, a driving lens (vibrating lens or scanning lens) IS1, a lens 13, and a lens array LA. The lenses 11 and 12 are included in a relay lens unit (relay optical system, lens unit) that forms an intermediate image (first intermediate image) IM1 by using light from a light source. In this example, the driving lens IS1 corresponds to a first optical element, and the lens array LA corresponds to a second optical element. The lens array LA may be an integrally formed single element having a plurality of lens surfaces or may have a configuration in which a plurality of lenses are individually arranged. In the latter case, the plurality of lenses are collectively referred to as one optical element (second optical element).

The driving lens IS1 can be rotated about an optical axis in a state where the driving lens IS1 is decentered from the optical axis OA, and its decentered amount from the optical axis OA is variable. In this example, the decentered amount from the optical axis OA of the driving lens IS1 is substantially unchanged during one rotation of rotational scanning using the light beam. In this example, the driving lens IS1 has a configuration similar to a configuration of a lens of an image stabilizing unit (image stabilizing lens), but is not driven for reducing image blur caused by camera shake and is driven for performing the rotational scanning using the light beam. Therefore, a frequency of the rotational scanning using the light beam performed by driving the driving lens IS1 is set to a frequency higher than a frequency of camera shake (10 Hz or less) and is set to, for example, 20 to 100 Hz. These are similar in driving lenses IS2, IS3, and IS4 according to each example described below.

As the object surface OP, a light source such as a laser diode that emits the light beam is disposed. The light beam from the light source passes through the first lens 11, is reflected by a reflective surface R1, passes through the second lens 12, and forms an intermediate image (first intermediate image) IM1. An angle (reflection angle) on the reflective surface R1 is not limited to the angle illustrated in FIG. 2.

In this example, the light beam from the lens 11 is reflected by the reflective surface R1 and enters the lens 12, but the present invention is not limited to this. For example, the light beam from the lens 11 may directly enter the lens 12 without passing through a reflective surface. Even in this case, a prism (separation surface) for separating a reflected light from a retina and guiding the reflected light to a detector (refer to FIG. 7) is disposed. This point is similar in each example described below.

After forming the intermediate image IM1, the light beam enters the driving lens IS1. A driving unit (refer to FIG. 7) can perform rotational scanning using the light beam (shift and decenter the light beam) by rotationally driving the driving lens IS1 so as to generate a ring-shaped light beam. The ring-shaped light beam passes through the lens 13 and the lens array LA, forms an intermediate image (second intermediate image) IM2, and then is incident on the projection surface PP, that is, the retina (fundus) of an eye. That is, the light beam having passed through the lens array LA forms the intermediate image IM2 and thereafter is incident on the projection surface PP.

This example uses, as the second optical element, the lens array LA including a plurality of lenses arranged in a ring shape (disposed around the optical axis OA). In a case where the lens array LA is used, a detected signal is a discrete signal (discontinuous signal), but if the lens array LA is used, it is possible to shorten a focal length of each lens included in the lens array LA. That is, if the lens array LA is not used, it is necessary to dispose a lens having a focal length in accordance with a tilt of the light beam that has passed through the relay lens unit, and the intermediate image moves to an image side, which extends the optical path. Further, in this example, the optical path can be shortened by disposing the lens 13 in the optical path between the driving lens IS1 and the lens array LA.

In this example, the following inequality (1) may be satisfied where S represents a decentered amount (parallel decentered amount, i.e., a distance in a vertical direction from the optical axis OA) of the driving lens IS1, and L represents a radius of the intermediate image IM2.

$$5 \leq L/S \tag{1}$$

If the value is smaller than the lower limit of the inequality (1), the ring of the light beam on the retina becomes too small and measurement accuracy decreases.

The numerical range of the inequality (1) may be set to a numerical range of the following inequality (1a).

$$7 \leq L/S \leq 25 \tag{1a}$$

If the value is larger than the upper limit of the inequality (1a), the optical system OS1 becomes large.

The numerical range of the inequality (1a) may be set to a numerical range of the following inequality (1b).

$$7 \leq L/S \leq 20 \tag{1b}$$

The inequalities (1), (1a), and (1b) may be satisfied in Examples 2, 3, and 5 described below.

This example uses, instead of the conventional spinning tilted mirror, the driving lens IS1 to perform the rotational scanning using the light beam. As a result, it is possible to shorten the optical path length and to reduce the size of the optical system (projection optical system) of the inspection apparatus.

In this example, the first optical element is the driving lens IS1 having a variable decentered amount from the optical axis OA, but is not limited to this. For example, the first optical element may be a shift lens that can be rotated about the optical axis in a state where the first optical element is decentered from the optical axis OA with its decentered amount unchanged or may be a tilt lens that can be rotated about the optical axis. Here, the tilt lens is a lens in which a normal line in a section including the optical axis OA (on the optical axis is tilted with respect to (is not parallel to) the optical axis OA. This point is similar in Examples 2, 3, and 5 described below.

EXAMPLE 2

Figure 3:
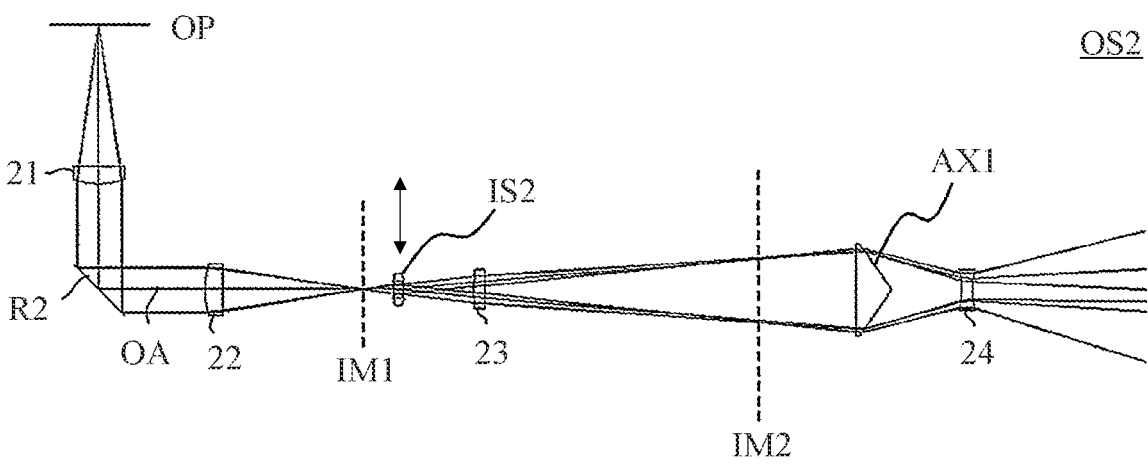
FIG. 3 is a sectional view of an optical system according to Example 2.

Next, a description is given of an optical system OS2 according to Example 2 of the present invention, with reference to FIG. 3. FIG. 3 is a sectional view of the optical system OS2. The optical system OS2 differs from the optical system OS1 according to Example 1 in that the optical system OS2 includes an axicon lens AX1 and a concave lens 24 instead of the lens array LA.

The optical system OS2 includes, in an order from an object surface side to a projection surface side (target side), a lens (first lens) 21, a reflective surface R2, a lens (second lens) 22, a driving lens IS2, a lens 23, the axicon lens AX1, and the concave lens 24. The lenses 21 and 22 are included in a relay lens unit (relay optical system, lens unit) that forms an intermediate image (first intermediate image) IM1 by using light from a light source. In this example, the driving lens IS2 corresponds to the first optical element, and the axicon lens AX1 and the concave lens 24 correspond to the second optical element.

As an object surface OP, a light source such as a laser diode that emits a light beam is disposed. As in Example 1, the light beam from the light source passes through the lens 21 of the relay lens unit, is reflected by the reflective surface R2, passes through the lens 22 of the relay lens unit, and forms an intermediate image (first intermediate image) IM1.

After forming the intermediate image IM1, the light beam enters the driving lens IS2. A driving unit (refer to FIG. 7) can perform rotational scanning using the light beam (shift and decenter the light beam) by rotationally driving the driving lens IS2 so as to generate a ring-shaped light beam. After forming an intermediate image (second intermediate image) IM2, the ring-shaped light beam passes through the axicon lens AX1 and the concave lens 24 and then is incident on a projection surface PP, that is, a retina (fundus) of an eye.

In this example, the axicon lens AX1 has a function of making a direction of the incident light beam close to a direction of the center. In a case where the axicon lens AX1 is used, a continuous signal can be detected unlike the case where the lens array LA is used as in Example 1. If the concave lens 24 is disposed on the projection surface side of the axicon lens AX1, it is possible to expand the light beam on the projection surface PP and to measure fundi of both eyes of a subject at the same time.

EXAMPLE 3

Figure 4:
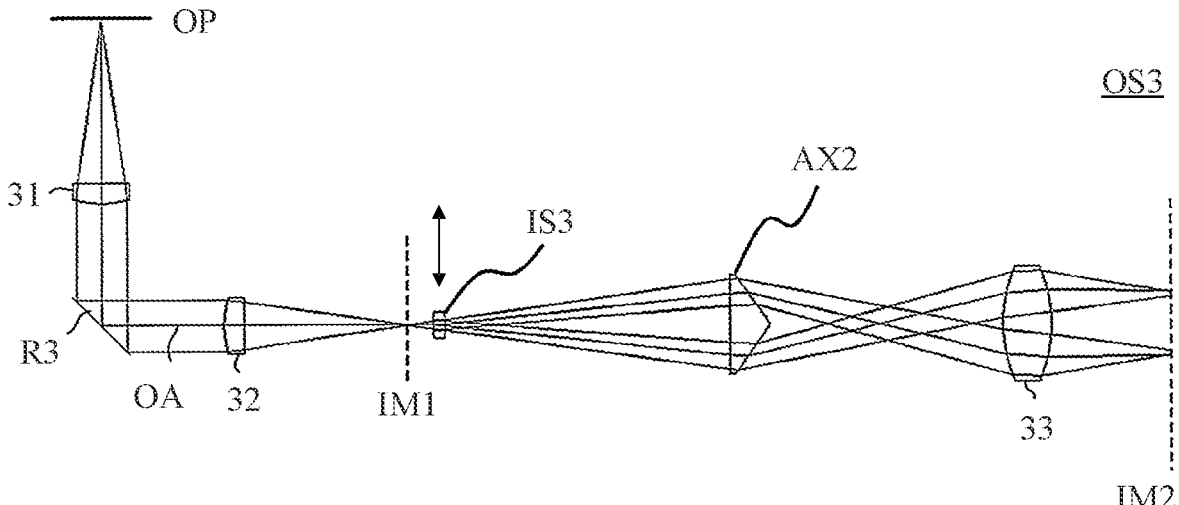
FIG. 4 is a sectional view of an optical system according to Example 3.

Next, a description is given of an optical system OS3 according to Example 3 of the present invention, with reference to FIG. 4. FIG. 4 is a sectional view of the optical system OS3. The optical system OS3 differs from the optical system OS2 according to Example 2 in that the optical system OS3 includes a convex lens 33 on a projection surface side (target side) of an axicon lens AX2.

The optical system OS3 includes, in an order from an object surface side to a projection surface side, a lens (first lens) 31, a reflective surface R3, a lens (second lens) 32, a driving lens IS3, the axicon lens AX2, and the convex lens 33. The lenses 31 and 32 are included in a relay lens unit (relay optical system, lens unit) that forms an intermediate image (first intermediate image) MI by using light from a light source. In this example, the driving lens IS3 corresponds to the first optical element, and the axicon lens AX2 and the convex lens 33 correspond to the second optical element.

As an object surface OP, a light source such as a laser diode that emits a light beam is disposed. As in Example 1, the light beam from the light source passes through the lens 31 of the relay lens unit, is reflected by the reflective surface R3, passes through the lens 32 of the relay lens unit, and forms an intermediate image (first intermediate image) IM1.

After forming the intermediate image IM1, the light beam enters the driving lens IS3, A driving unit (refer to FIG. 7) can perform rotational scanning using the light beam (shift and decenter the light beam) by rotationally driving the driving lens IS3 so as to generate a ring-shaped light beam. The ring-shaped light beam passes through the axicon lens AX2 and the convex lens 33, forms an intermediate image (second intermediate image) IM2, and then is incident on a projection surface PP, that is, a retina (fundus) of an eye.

The optical system OS3 of this example uses the axicon lens AX2 to properly bend the light beam and uses the convex lens 33 to form the intermediate image IM2 and to make a principal ray of the light beam substantially parallel. As a result, the light beam having passed through the convex lens 33 forms the intermediate image IM2 and thereafter is incident on the projection surface PP. The axicon lens AX2 in this example is a convex axicon lens, but is not limited to this, and may be a concave axicon lens.

EXAMPLE 4

Figure 5:
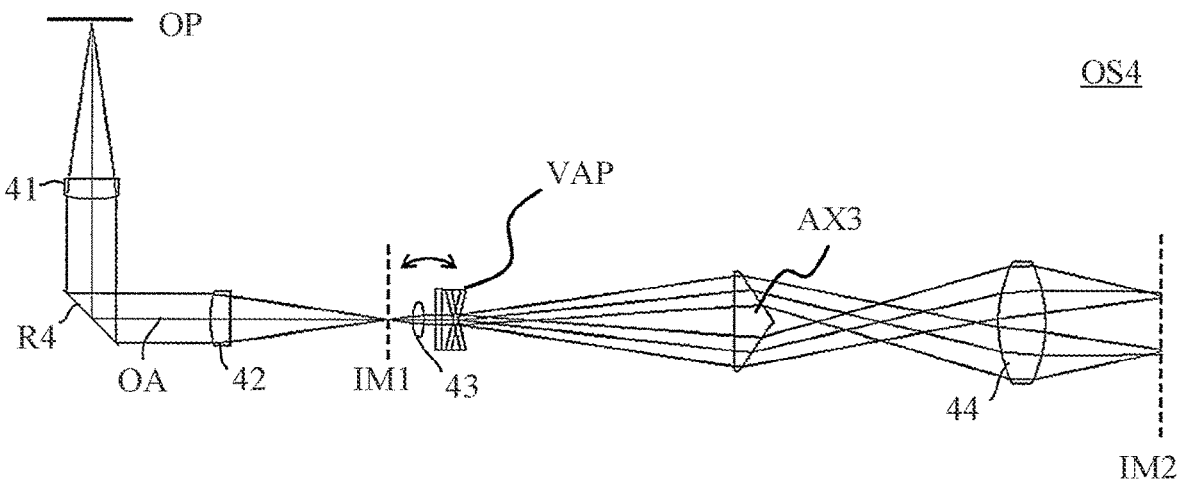
FIG. 5 is a sectional view of an optical system according to Example 4.

Next, a description is given of an optical system OS4 according to Example 4 of the present invention, with reference to FIG. 5. FIG. 5 is a sectional view of the optical system OS4. The optical system OS4 differs from the optical system OS3 according to Example 3 in that the optical system OS4 includes a lens 43 and a variable apex-angle prism VAP instead of the driving lens IS3.

The optical system OS4 includes, in an order from an object surface side to a projection surface side (target side), a lens (first lens) 41, a reflective surface R4, a lens (second lens) 42, the lens 43, the variable apex-angle prism YAP, an axicon lens AX3, and a lens 43. The lenses 41 and 42 are included in a relay lens unit (relay optical system, lens unit) that forms an intermediate image (first intermediate image) IM1 by using light from a light source. In this example, the variable apex-angle prism YAP corresponds to the first optical element, the axicon lens AX3 and the lens 43 correspond to the second optical element.

As an object surface OP, a light source such as a laser diode that emits a light beam is disposed. As in Example 1, the light beam from the light source passes through the lens 41 of the relay lens unit and is reflected by the reflective surface R4, passes through the lens 42 of the relay lens unit, and forms the intermediate image IM1.

After forming the intermediate image IM1, the light beam passes through the lens 43 and enters the variable apex-angle prism YAP. An unillustrated driving unit drives the variable apex-angle prism YAP so as to change an apex angle of the variable apex-angle prism YAP. By changing the apex angle of the variable apex-angle prism YAP, it is possible to perform rotational scanning using the light beam and to generate a ring-shaped light beam. In this example, the apex angle of the variable apex-angle prism YAP is substantially unchanged during one rotation of the rotational scanning using the light beam. The ring-shaped light beam passes through the axicon lens AX3 and the convex lens 44, forms an intermediate image IM2, and then is incident on a projection surface PP, that is, a retina (fundus) of an eye.

According to this example, the ring-shaped light beam can be generated by controlling the apex angle of the variable apex-angle prism YAP without shifting and decentering the driving lens IS3 as in Example 3. The axicon lens AX3 in this example is a convex axicon lens, but is not limited to this, and may be a concave axicon lens.

In this example, the first optical element is the variable apex-angle prism YAP, but is not limited to this, and may be, for example, a prism that can be rotated about the optical axis.

EXAMPLE 5

Figure 6:
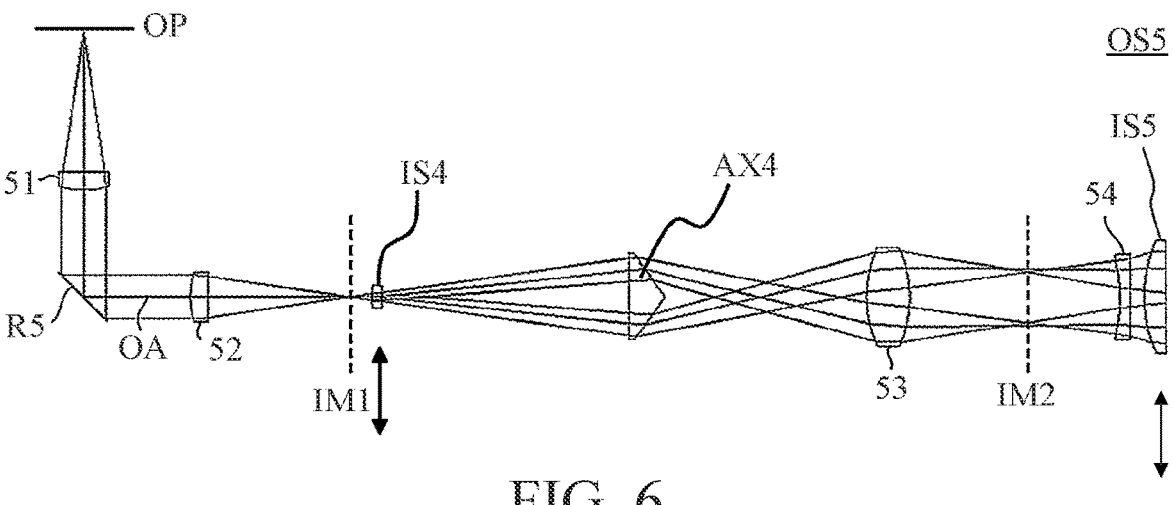
FIG. 6 is a sectional view of an optical system according to Example 5.

Next, a description will be given of an optical system OS5 according to Example 5 of the present invention with reference to FIG. 6. FIG. 6 is a sectional view of the optical system OS5. The optical system OS5 differs from the optical system OS3 according to Example 3 in that the optical system OS5 includes a concave lens 54 and a convex image stabilizing lens IS5 between an intermediate image IM2 and a projection surface PP. The image stabilizing lens IS5 is a lens movable in a direction intersecting an optical axis OA (a direction including a component orthogonal to the optical axis OA) and performs image stabilization while being driven at a frequency of, for example, 10 Hz or less so that image blur caused by camera shake is reduced.

The optical system OS5 includes, in an order from an object surface side to a projection surface side (target side), a lens (first lens) 51, a reflective surface R5, a lens (second lens) 52, a driving lens IS4, an axicon lens AX4, a convex lens 53, the concave lens 54, and the convex image stabilizing lens IS5. The lenses 51 and 52 are included in a relay lens unit (lens unit) that forms an intermediate image (first intermediate image) IM1 by using light from a light source. In this example, the driving lens IS4 corresponds to the first optical element, and the axicon lens AX4, the convex lens 53, the concave lens 54, and the image stabilizing lens IS5 correspond to the second optical element.

As an object surface OP, a light source such as a laser diode that emits a light beam is disposed. As in Example 3, the light beam from the light source passes through the lens 51 of the relay lens unit, reflected by the reflective surface R5, passes through the lens 52 of the relay lens unit, and forms an intermediate image (first intermediate image) IM1. Further, as in Example 3, after forming the intermediate image IM1, the light beam enters the driving lens IS4. A driving unit (refer to FIG. 7) can perform rotational scanning using the light beam (shift and decenter the light beam) by rotationally driving the driving lens IS4 so as to generate a ring-shaped light beam. The ring-shaped light beam passes through the axicon lens AX4 and the convex lens 53 and forms the intermediate image (second intermediate image) IM2. The axicon lens AX4 in this example is a convex axicon lens, but is not limited to this, and may be a concave axicon lens.

After forming the intermediate image IM2, the light beam passes through the concave lens 54 and the convex image stabilizing lens IS5 and then is incident on the projection surface PP, that is, a retina (fundus) of an eye.

In the optical system OS5 of this example, the concave lens 54 and the convex image stabilizing lens IS5 are disposed between the intermediate image IM2 and the projection surface PP. In a case where only the concave lens 54 is disposed there, the light can be spread on the projection surface PP (on the retina), but the ring formed as the intermediate image IM2 becomes small on the retina. On the other hand, in a case where only the convex image stabilizing lens IS5 is disposed there, it is possible to prevent the ring formed as the intermediate image IM2 from becoming small on the retina, but the spread of light on the projection surface PP becomes small. Therefore, by disposing the concave lens 54 and the convex image stabilizing lens IS5 having focal lengths close to each other (for example, having the same focal length) side by side, image stabilization can be performed while their disadvantages are compensated for by each other. In this example, the convex lens is used as the image stabilizing lens IS5, but the present invention is not limited to this, and the concave lens 54 may be used as an image stabilizing lens to perform image stabilization.

Numerical Examples 1 to 5 respectively corresponding to Examples 1 to 5 are given below.

In each numerical example, a surface number indicates a surface number i that is counted from an object surface side. R (mm) indicates a curvature radius of an i-th surface, and D (mm) indicates a distance (distance on an optical axis) between the i-th surface and an (i+1)-th surface, Nd and vd respectively indicate a refractive index and an Abbe number at a d line (587.6 nm) of medium between the i-th surface and the (i+1)-th surface. The Abbe number vd is expressed by the following equation, where NF and NC respectively indicate refractive indexes at an F line (486.1 nm) and a C line (656.3 nm) of the medium between the i-th surface and the (i+1) surface.

$$vd=(Nd-1)/(NF-NC)$$

A parallel decentered amount S is defined as a distance from a z-axis in a vertical direction on each surface. A tilt decentered amount T is defined as an amount of rotation about a direction orthogonal to the z-axis on each surface. A tilt decentered rotation position T0 is defined as a distance in a z direction from an origin to a rotational center of each surface in a state where the tilt decentered amount T is applied to each surface.

An axicon lens is expressed by the following equation, where C represents an aspherical coefficient.

$$z=Cr$$

r is expressed by the following equation.

$$r=\sqrt{x^2+y^2}$$

Here, it is assumed that an optical axis is the z-axis, and a direction from an object surface to a projection surface is positive (+ z-direction). Further, it is assumed that an axis orthogonal to the z-axis is a y-axis, and an axis orthogonal to the z-axis and the y-axis is an x-axis.

Numerical Example 1

| Surface Number | R | D | Nd | vd |
|---|---|---|---|---|
| 1 OP | ∞ | −40.0 | | |
| 2 11 | ∞ | −5.0 | 1.516 | 64.14 |
| 3 11 | 23.0 | −30.0 | | |
| 4 R1 | ∞ | 30.0 | | |
| 5 12 | 23.0 | 5.0 | 1.516 | 64.14 |
| 6 12 | ∞ | 46.0 | | |
| 7 IS | 8.0 | 3.0 | 1.516 | 64.14 |
| 8 IS | −8.0 | 70.0 | | |
| 9 13 | −18.0 | 10.0 | 1.516 | 64.14 |
| 10 13 | ∞ | 57.0 | | |
| 11 LA | 15.0 | 12.0 | 1.516 | 64.14 |
| 12 LA | −10.0 | 530.0 | | |
| 13 PP | ∞ | 0.0 | | |

7 and 8-th Surfaces

S = 1

11 and 12-th Surfaces

S = 9

Numerical Example 2

| Surface Number | R | D | Nd | vd |
|---|---|---|---|---|
| 1 OP | ∞ | −40.0 | | |
| 2 21 | ∞ | −5.0 | 1.516 | 64.14 |
| 3 21 | 23.0 | −30.0 | | |
| 4 R2 | ∞ | 30.0 | | |
| 5 22 | 23.0 | 5.0 | 1.516 | 64.14 |
| 6 22 | ∞ | 48.3 | | |
| 7 IS | 9.6 | 3.0 | 1.516 | 64.14 |
| 8 IS | −10.0 | 20.0 | | |
| 9 2.3 | ∞ | 3.0 | 1.516 | 64.14 |
| 10 23 | 51.6 | 106.0 | | |
| 11 AX1 | ∞ | 10.0 | 1.459 | 67.80 |
| 12 AX1 | ∞ | 24.0 | | |
| 13 24 | −18.0 | 4.0 | 1.847 | 23.78 |
| 14 24 | 18.0 | 500.0 | | |
| 15 PP | ∞ | 0.0 | | |

Axicon Lens 12-th Surface

C = -0.75

7 and 8-th Surfaces

S = 1

US 12,569,133 B2

9

Numerical Example 3

| Surface Number | R | D | Nd | vd |
|---|---|---|---|---|
| 1 OP | ∞ | -40.0 | | |
| 2 31 | ∞ | -5.0 | 1.516 | 64.14 |
| 3 31 | 23.0 | -30.0 | | |
| 4 R3 | ∞ | 30.0 | | |
| 5 32 | 23.0 | 5.0 | 1.516 | 64.14 |
| 6 32 | ∞ | 46.0 | | |
| 7 IS | 9.0 | 3.0 | 1.516 | 64.14 |
| 8 IS | -10.0 | 70.0 | | |
| 9 AX2 | ∞ | 10.0 | 1.459 | 67.80 |
| 10 AX2 | ∞ | 57.0 | | |
| 11 33 | 35.0 | 12.0 | 1.516 | 64.14 |
| 12 33 | -35.0 | 530.0 | | |
| 13 PP | ∞ | 0.0 | | |

Axicon Lens 10-th Surface

C = -0.7
7 and 8-th Surfaces

S = 1

Numerical Example 4

| Surface Number | R | D | Nd | vd |
|---|---|---|---|---|
| 1 OP | ∞ | -40.0 | | |
| 2 41 | ∞ | -5.0 | 1.516 | 64.14 |
| 3 41 | 23.0 | -30.0 | | |
| 4 R4 | ∞ | 30.0 | | |
| 5 42 | 23.0 | 5.0 | 1.516 | 64.14 |
| 6 42 | ∞ | 46.0 | | |
| 7 43 | 9.0 | 3.0 | 1.516 | 64.14 |
| 8 43 | -10.0 | 3.0 | | |
| 9 VAP | ∞ | 1.4 | 1.516 | 64.14 |
| 10 VAP | ∞ | 3.0 | 1.417 | 52.20 |
| 11 VAP | ∞ | 1.4 | 1.516 | 64.14 |
| 12 VAP | ∞ | 70.0 | | |
| 13 AX3 | ∞ | 10.0 | 1.459 | 67.80 |
| 14 AX3 | ∞ | 57.0 | | |
| 15 44 | 35.0 | 12.0 | 1.516 | 64.14 |
| 16 44 | -35.0 | 530.0 | | |
| 17 PP | ∞ | 0.0 | | |

Axicon Lens 14-th Surface

C = -0.7
11-th Surface

T = 14°
T0 = 0.7
12-th Surface

T = 14°
T = -0.7

Numerical Example 5

| Surface Number | R | D | Nd | vd |
|---|---|---|---|---|
| 1 OP | ∞ | -40.0 | | |
| 2 51 | ∞ | -5.0 | 1.516 | 64.14 |
| 3 51 | 23.0 | -30.0 | | |
| 4 R5 | ∞ | 30.0 | | |
| 5 52 | 23.0 | 5.0 | 1.516 | 64.14 |
| 6 52 | ∞ | 46.0 | | |
| 7 IS | 9.0 | 3.0 | 1.516 | 64.14 |

10

-continued

| | | | | |
|---|---|---|---|---|
| 8 IS | -10.0 | 70.0 | | |
| 9 AX4 | ∞ | 10.0 | 1.459 | 67.80 |
| 10 AX4 | ∞ | 57.0 | | |
| 11 53 | 35.0 | 12.0 | 1.516 | 64.14 |
| 12 53 | -35.0 | 60.0 | | |
| 13 54 | -40 | 3.0 | 1.516 | 64.14 |
| 14 54 | ∞ | 4.0 | | |
| 15 IS | 40.0 | 6.0 | 1.516 | 64.14 |
| 16 IS | ∞ | 500.0 | | |
| 17 PP | ∞ | 0.0 | | |

Axicon Lens 10-th Surface

C = -0.7
7 and 8-th Surfaces

S = 1

The following Table 1 gives values of the inequality (1) in each numerical example.

TABLE 1

| | DECENTERED AMOUNT S | RADIUS L | L/S |
|---|---|---|---|
| EXAMPLE 1 | 1 mm | 11.1 mm | 11.1 |
| EXAMPLE 2 | 1 mm | 8 mm | 8 |
| EXAMPLE 3 | 1 mm | 10 mm | 10 |
| EXAMPLE 4 | 0.7 deg | 9.5 mm | — |
| EXAMPLE 5 | 1 mm | 10 mm | 10 |

Inspection Apparatus

Figure 7:
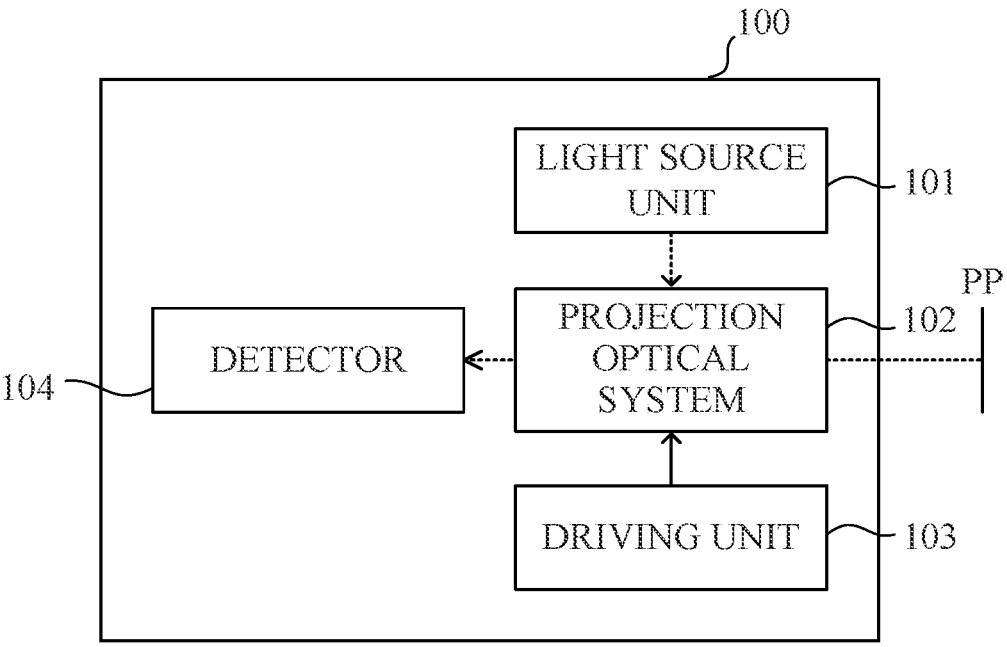
FIG. 7 is a block diagram of an inspection apparatus including an optical system according to each example.

Next, a description is given of an inspection apparatus (fixation measuring apparatus) 100 with reference to FIG. 7. FIG. 7 is a block diagram illustrating the inspection apparatus 100. The inspection apparatus 100 can detect a state of a target (eyeball) by detecting a change in polarization between an incident light toward the target and reflected light from the target (detect a fixation state of the eyeball by identifying a central fovea of a retina of the eyeball).

The inspection apparatus 100 includes a light source unit 101, a projection optical system 102, a driving unit 103, and a detector (detection optical system) 104. The light source unit 101 includes a light source such as a laser diode and emits a light beam toward the projection optical system 102. The projection optical system 102 corresponds to any of the optical systems OS1 to OS5 according to Examples 1 to 5. In order to perform rotational scanning using the light beam, the driving unit 103 drives the driving lens so as to shift and decenter the driving lens in a case where any of the optical systems according to Examples 1 to 3 and 5 is used, and drives the variable apex-angle prism so as to change the apex angle of the variable apex-angle prism in a case where the optical system according to Example 4 is used. The detector 104 detects the reflected light reflected by the retina (fundus) of the eye on the projection surface PP. The detector 104 also detects a change in polarization between the incident light toward the retina and the reflected light from the retina.

According to each example, since an optical element that transmits a light beam is used for performing rotational scanning using the optical beam, it is possible to shorten an optical path length and to provide a small optical system and a small inspection apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-089810, filed on May 28, 2021 which is hereby incorporated by reference herein in its entirety.

What is claimed is:

1. An optical system comprising:
a lens unit configured to form a first intermediate image by using light from a light source;
a first optical element configured to transmit the light from the first intermediate image and to move to rotationally scan a target; and
a second optical element configured to guide the light from the first optical element to the target, wherein the second optical element is an axicon lens.

2. The optical system according to claim 1, wherein the first optical element can be rotated about an optical axis in a state where the first optical element is decentered from the optical axis, and a decentered amount from the optical axis of the first optical element is variable.

3. The optical system according to claim 2, wherein the decentered amount from the optical axis of the first optical element is unchanged during one rotation of rotational scanning using the light.

4. The optical system according to claim 1, wherein the first optical element can be rotated about an optical axis in a state where the first optical element is decentered from the optical axis by an unchanged decentered amount.

5. The optical system according to claim 2, wherein a following inequality is satisfied:

$$5 \le L/S$$

where S represents the decentered amount from the optical axis of the first optical element, and L represents a radius of a second intermediate image that is formed at a position closer to a projection surface than the first intermediate image.

6. The optical system according to claim 1, wherein the first optical element is a tilt lens that can be rotated about the optical axis.

7. The optical system according to claim 1, wherein the first optical element is a variable apex-angle prism.

8. The optical system according to claim 7, wherein an apex angle of the variable apex-angle prism is unchanged during one rotation of rotational scanning using the light.

9. The optical system according to claim 1, wherein the first optical element is a prism that can be rotated about an optical axis.

10. The optical system according to claim 1, wherein the second optical element is a lens array including a plurality of lenses that are disposed around an optical axis.

11. The optical system according to claim 10, wherein the light having passed through the second optical element forms a second intermediate image and thereafter is incident on the target.

12. The optical system according to claim 1, further comprising a concave lens disposed at a position closer to the target than the second optical element.

13. The optical system according to claim 1, further comprising a convex lens disposed at a position closer to the target than the second optical element.

14. The optical system according to claim 13, wherein the light having passed through the convex lens forms a second intermediate image and thereafter is incident on the target.

15. The optical system according to claim 13, further comprising a lens movable in a direction including a component orthogonal to an optical axis,
wherein the lens performs image stabilization by moving at a frequency of 10 Hz or less.

16. The optical system according to claim 15, wherein the light having passed through the convex lens forms a second intermediate image and thereafter is incident on the lens.

17. The optical system according to claim 1, wherein a frequency of rotational scanning using the light is 20 to 100 Hz, the rotational scanning is performed by driving the first optical element.

18. An inspection apparatus comprising:
an optical system including:
a lens unit configured to form a first intermediate image by using light from a light source;
a first optical element configured to transmit the light from the first intermediate image and to move to rotationally scan a target; and
a second optical element configured to guide the light from the first optical element to the target, wherein the second optical element is an axicon lens; and
a detector configured to detect reflected light from the target.

19. The inspection apparatus according to claim 18, wherein the detector detects a state of the target by detecting a change relating to polarization between incident light toward the target and the reflected light from the target.

20. The inspection apparatus according to claim 18, wherein the target is an eyeball.

21. The inspection apparatus according to claim 20, the detector detects a fixation state of the eyeball by identifying a central fovea of a retina of the eyeball.

* * * * *